(12) United States Patent
Al Dandachi Atassi

(10) Patent No.: US 9,089,477 B2
(45) Date of Patent: *Jul. 28, 2015

(54) STORAGE-STABLE FORMULATION OF PARACETAMOL IN AQUEOUS SOLUTION

(75) Inventor: Khaled Al Dandachi Atassi, Brussels (BE)

(73) Assignee: NEOGEN N.V., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/984,132

(22) PCT Filed: Feb. 10, 2011

(86) PCT No.: PCT/EP2011/051971
§ 371 (c)(1),
(2), (4) Date: Aug. 7, 2013

(87) PCT Pub. No.: WO2012/107093
PCT Pub. Date: Aug. 16, 2012

(65) Prior Publication Data
US 2013/0317112 A1    Nov. 28, 2013

(51) Int. Cl.
*A61K 31/16* (2006.01)
*A61K 9/00* (2006.01)
*A61K 31/166* (2006.01)

(52) U.S. Cl.
CPC .............. *A61K 9/0019* (2013.01); *A61K 31/166* (2013.01)

(58) Field of Classification Search
USPC ................................................ 514/613, 615
See application file for complete search history.

(56) References Cited

U.S. PATENT DOCUMENTS 6,992,218 B2 * 1/2006 Dietlin et al. .................... 564/4
8,404,748 B2 * 3/2013 Al Dandachi Atassi ...... 514/629
8,404,891 B2 * 3/2013 Al Dandachi Atassi .......... 564/4
2004/0054012 A1    3/2004 Dietlin et al.
2009/0143474 A1 * 6/2009 Royal et al. .................... 514/629

FOREIGN PATENT DOCUMENTS

| CN | 1556694 A | 12/2004 |
|----|-----------|---------|
| EP | 1752139 A1 | 2/2007 |
| FR | 2751875 A1 | 2/1998 |
| FR | 2809619 A1 | 12/2001 |
| WO | WO 2009/081283 A2 | 7/2009 |
| WO | WO 2011/018522 A1 | 2/2011 |
| WO | WO 2011/071400 A1 | 6/2011 |

OTHER PUBLICATIONS

International Search Report and Written Opinion of the International Searching Authority for International Application No. PCT/EP2011/051971, mailed on Nov. 2, 2011.
Database WPI Week 200923, Thomson Scientific, London, GB; An 2009-G02209, XP002661986, and CN 101 366 695 A (Jiangsiu-Sihuan Biological CO LTD) (Feb. 18, 2009).

* cited by examiner

*Primary Examiner* — Paul Zarek
*Assistant Examiner* — George W Kosturko
(74) *Attorney, Agent, or Firm* — Knobbe, Martens, Olson & Bear, LLP

(57) ABSTRACT

The present invention relates to a method for the production of a formulation that is stable to oxidation and that is based on paracetamol in an aqueous solvent, comprising the steps of (i) dissolving paracetamol in an aqueous solvent comprising an isotonic agent that is sodium chloride and a buffer agent that is sodium citrate, having a temperature between 65° C. and 95° C. and having pH between 5.0 and 6.0 in a reaction vessel, (ii) replacing the remaining air in the vessel by an inert gas, such as nitrogen, and cooling the solution so formed to a temperature below 38° C., (iii) adding cysteine hydrochloride to the solution without mechanical agitation, and (iv) closing the reaction vessel and mechanically agitating the solution in a nitrogen atmosphere. The further relates to a formulation prepared according to the method.

11 Claims, No Drawings

STORAGE-STABLE FORMULATION OF PARACETAMOL IN AQUEOUS SOLUTION

CROSS-REFERENCE TO RELATED APPLICATIONS

This application is the U.S. National Phase under 35 U.S.C. §371 of International Application PCT/EP2011/051971, filed Feb. 10, 2011.

TECHNICAL FIELD OF THE INVENTION

The object of the present invention is a new method for producing injectable aqueous solutions containing paracetamol, and a formulation based on the method.

BACKGROUND TO THE INVENTION

Paracetamol (INN of acetaminophen or N-(4-hydroxyphenyl)acetamide) is an analgesic and an antipyretic widely used in hospitals. It is desirable to have available stable liquid pharmaceutical formulations of this active principle for administration by injection, in particular for intravenous infusion.

It is known that paracetamol in aqueous solution is liable to undergo hydrolysis to form p-aminophenol, which is itself liable to degrade into quinoneimine (cf. for example J. E. Fairbrother, "Acetaminophen" in Analytical Profiles of Drug Substances, 1974, vol. 3, pp. 1-109). The rate of degradation of paracetamol increases with increasing temperature and light. This rate is minimal at a pH in the region of 6 (K. T. Koshy et al., 1961, J. Pharm. Sci. 50, pp. 116-118).

It is known practice to add a buffer and an antioxidant or free-radical scavenger to stabilize paracetamol in solution.

WO 02/072 080, for example, describes stable aqueous paracetamol solutions for infusion comprising a buffer of pH 5.5 to 6.5 and an antioxidant chosen from ascorbic acid and a derivative bearing a thiol function.

EP 0 916 347 discloses-paracetamol solutions based on a mixture of water and of alcoholic solvents comprising a buffer of pH 5.5 to 5.6 and metabisulfite as antioxidant.

EP 0 859 329 describes a deoxygenation process by which the aqueous solvent is deoxygenated by bubbling into an inert gas, such as nitrogen.

Also US 2004/0054012 describes a deoxygenation process involving the bubbling of an inert gas such as nitrogen through the aqueous solution.

WO 2008/135601 describes aqueous paracetamol solutions for infusion prepared using high temperatures and in an oxygen-free environment.

Some of the prior-art stabilized injectable solutions of paracetamol have the drawback of requiring the total absence of oxygen during the production process. However, oxygen shows a very great facility to dissolve in water, making it necessary to ensure that the solution, once deoxygenated, does not subsequently come into contact with atmospheric air at every stage in the production process. The methods of the art, therefore, require a considerable amount of time, care, and the use of specialised equipment and/or protocols. Even with all these precautions, total absence of oxygen can never be ensured during all the preparatory steps. In presence of even traces of oxygen, degradation products can be generated which increase in quantity during storage of the product, and ultimately leads to a reduced shelf-life.

The main object of the present invention is to provide a formulation and a method for aqueous formulations of paracetamol, which can notably be utilized in injectable preparations being stable over a long period, which solves the problems in view of the problems of the art.

SUMMARY OF SOME EMBODIMENTS OF THE INVENTION

One embodiment of the present invention relates to a method for the production of a formulation that is stable to oxidation and that is based on paracetamol in an aqueous solvent, comprising the steps of:
(i) dissolving paracetamol in an aqueous solvent comprising an isotonic agent that is sodium chloride and a buffer agent that is sodium citrate, having a temperature between 65° C. and 95° C. and having pH between 5.0 and 6.0 in a reaction vessel,
(ii) replacing the remaining air in the vessel by an inert gas, such as nitrogen, and cooling the solution so formed to a temperature below 38° C.,
(iii) adding cysteine hydrochloride to the solution without mechanical agitation, and
(iv) closing the reaction vessel and mechanically agitating the solution in a nitrogen atmosphere.

The aqueous solvent and/or solution may not be purged with an inert gas. The inert gas may be nitrogen or helium. The aqueous solvent may have a temperature between 70° C. and 90° C. and preferably between 80° C. and 85° C. The aqueous solvent may have a pH between 5.6 and 5.7, and preferably of 5.5. The paracetamol may be present in the final solution in an amount of between 0.25 and 2% (w/v). The sodium chloride may be present in the final solution in an amount of between 0.5 and 0.9% (w/v). The sodium citrate may be present in the final solution in an amount of between 0.05 and 0.09% (w/v). The sodium citrate may be monosodium citrate that is anhydrous, monohydrate, dehydrate or trihydrate. The paracetamol may be added to the aqueous solvent in step (i) without mechanical agitation. The solution may be stirred after replacing the remaining air in the vessel by the inert gas such as nitrogen in step (ii). The solution in step (iv) may be subsequently filtered prior to packaging in one or more vials. The vials may be closed under vacuum.

Another embodiment of the invention relates to a formulation that is stable to oxidation and that is based on paracetamol in an aqueous solvent comprising:
between 0.25% and 2% (w/v) paracetamol,
between 0.5% and 0.9% (w/v) sodium chloride,
between 0.05% and 0.09% (w/v) monosodium citrate monohydrate,
between 0.015% and 0.035% (w/v) cysteine hydrochloride monohydrate, and
water for injection,
where the final pH of the formulation is between 5.0 and 6.0.
The water for injection may not be not degassed by bubbling with an inert gas. The formulation may be prepared according to a method as described herein.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

Throughout this application, the term "about" is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of items, and can also include 1.5, 2, 2.75 and 3.80, when referring to, for example, concentrations). The recitation of end points also includes the end point values themselves (e.g. from 1.0 to 5.0 includes both 1.0 and 5.0)

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The invention provides in a first aspect a liquid formulation that is stable to oxidation and that is based on paracetamol in an aqueous solvent. The formulation is characterized in that the paracetamol is admixed in the aqueous solvent having, as from the outset, a temperature between 65° C. and 95° C., preferably between 80° C. and 85° C. The pH of the aqueous solvent is between 5.0 and 6.0. The aqueous solvent is preferably not previously degassed by purging or bubbling with an insert gas such as nitrogen. Under a nitrogen atmosphere, the solution is subsequently cooled to a temperature below 38° C., preferably below 38° C. and equal to or above 5° C., 10° C., 15° C., 20° C., 25° C., or 30° C., after which cysteine hydrochloride is added without mechanical agitation. The addition is preferably rapid. The mixture is subsequently stirred in an atmosphere of nitrogen to yield a formulation of the invention.

Therefore, the invention provides in a first aspect a method for the production of a liquid formulation of paracetamol that is stable to oxidation, comprising the steps of:
i) dissolving paracetamol in an aqueous solvent having a temperature between 65° C. and 95° C., preferably between 80° C. and 85° C. and having pH between 5.0 and 6.0 in a reaction vessel,
ii) replacing the remaining air in the vessel by an inert gas, such as nitrogen, and cooling the solution so formed to a temperature below 38° C.,
iii) adding cysteine hydrochloride to the solution without mechanical agitation, and
iv) closing the reaction vessel, and mechanically agitating the solution in a nitrogen atmosphere.

As a result of the method, a liquid formulation of paracetamol that is stable to oxidation is provided.

The invention also relates to a liquid formulation obtainable by the method of the invention.

In a second aspect the invention provides a liquid formulation of paracetamol that is stable to oxidation obtainable by the following steps:
i) dissolving in a reaction vessel paracetamol in an aqueous solvent having a temperature between 65° C. and 95° C., preferably between 80° C. and 85° C. and having pH between 5.0 and 6.0,
ii) replacing the remaining air in the vessel by an inert gas, such as nitrogen, and cooling the solution so formed to a temperature below 38° C.,
iii) adding cysteine hydrochloride to the solution without mechanical agitation, and
iv) closing the reaction vessel, and mechanically agitating the solution in a nitrogen atmosphere.

As such, this method according to the present invention for the production of a formulation as defined herein involves the use of an aqueous solvent which is characterized by a high temperature (between 65° C. and 95° C., preferably between 80° C. and 85° C.) as from the outset, a cooling step (to below 38° C.), and the addition of cysteine hydrochloride. The cysteine hydrochloride is added without mechanical agitation such as stirring or shaking. It is preferably added rapidly. The above-mentioned steps are performed consecutively. It is to be appreciated that additional intervening steps may be present. For instance, the solution referred to in step iv) may be that of step iii); but other steps may be present between step iii) and step iv) such as a temperature change.

In an embodiment, the invention relates to a formulation and method as defined herein, wherein the aqueous solvent has, as from the outset, a temperature between 65° C. and 95°, preferably between 70° C. and 90°, most preferably between 80° C. and 85° C.

In another embodiment, the invention relates to a formulation and method as defined herein, wherein the aqueous solvent has a pH between 5.0 and 6.0, or 5.6 and 5.7, and preferably about 5.5.

In yet another embodiment, the invention relates to a formulation and method as defined herein, wherein the aqueous solvent comprises water, an isotonic agent and a buffer agent. The water is preferably water for injection. The water for injection is preferably not purged with an inert gas such as nitrogen or helium to remove or reduce dissolved oxygen. The aqueous solvent is preferably not purged with an inert gas such as nitrogen or helium to remove or reduce dissolved oxygen.

The aqueous solvent may be prepared by adding water for injection to a vessel at a temperature between 65° C. and 95°, preferably between 70° C. and 90°, most preferably between 80° C. and 85° C., adding isotonic agent (e.g. sodium chloride) and a buffer agent (e.g. sodium citrate). The addition is preferably rapid. The isotonic agent and a buffer agent are added without mechanical agitation. The air in the vessel is subsequently replaced with an inert gas (e.g. nitrogen or helium). The vessel is preferably subsequently closed and under placed under pressure of the inert gas. The mixture so formed is subsequently agitated mechanically under pressure of the inert gas. Mechanical agitation may proceed for about 5 minutes.

The invention further provides a formulation and method as defined herein wherein the paracetamol is present in the final formulation in an amount of (w/v) of 0.25%, 0.5%, 1%, 1.5%, 2%, 2.5%, 3%, or a value in the range between any two of the aforementioned values, preferably between 0.25 and 2%, preferably about 1%.

The paracetamol is preferably added to the aqueous solvent without mechanical agitation. The addition is preferably rapid. The air in the vessel is subsequently replaced with an inert gas (e.g. nitrogen or helium). The vessel is preferably subsequently closed and under placed under pressure of the inert gas. The mixture so formed is subsequently mechanically agitated under pressure of the inert gas. Mechanical agitation may proceed for about 5 minutes. During this time, the vessel may be allowed to cool towards the temperature defined in step (ii).

For the purpose of improving the stability of a liquid formulation of paracetamol, and thus to overcome the disadvantages described above, the present invention provides a method and a formulation which avoids minimising the oxygen in the aqueous solvent as from the outset, and oxygen is eliminated or reduced by temperature-controlled manufacturing wherein the temperature is initially set at and maintained within 65° C. and 95° C., preferably between 80° C. and 85° C. before cooling to a temperature of less than 38° C., preferably less than 38° C. and equal to or above 5° C., 10° C., 15° C., 20° C., 25° C., or 30° C., and cysteine hydrochloride is added after this cooling step. The invention therefore provides in a first aspect a liquid, stable to oxidation formulation based on paracetamol, while being able to be preserved for a prolonged period, characterized in that the paracetamol is admixed in the aqueous solvent having a temperature between 65° C. and 95° C., preferably between 80° C. and 85° C. and having a pH between 5.0 and 6.0, the solution is cooled to a temperature of less than 38° C., preferably less than 38° C. and equal to or above 5° C., 10° C., 15° C., 20° C., 25° C., or 30° C., and cysteine hydrochloride is added without mechanical agitation.

It is not essential to purge or bubble the aqueous solvent with inert gas such as nitrogen or helium as from the outset. As is understood in the art, purging with an inert gas such as nitrogen or helium removes or reduces dissolved oxygen. According to one aspect of the invention, the aqueous solvent used in step i) is not purged or bubbled with an inert gas, such as nitrogen. There may be no purging of the aqueous solvent before step i), or there may be no purging of the aqueous solvent during step i), or there may be no purging of the solution so formed after step i). Preferably, there is no purging before, during and after step i). Air in the reaction vessel is replaced with nitrogen after the addition of paracetamol and after the addition of cysteine hydrochloride. The nitrogen is preferably put under pressure. Eventually, the filling and packaging of the vials can also take place with the addition of an inert gas, such as nitrogen. The final solution may contain trace amounts of dissolved oxygen. Despite this, the paracetamol is still resistant to degradation for prolonged periods.

The invention relates to a formulation and method as defined herein, wherein the aqueous solvent comprises water, an isotonic agent and a buffer agent. The aqueous solvent may or may not have a low concentration of dissolved oxygen i.e. there is no requirement to purge the aqueous solvent with an inert gas such as nitrogen.

The buffer agent may be chosen from citrate buffer, phosphate buffer, phosphate-citrate buffer, bicarbonate buffer, tartrate buffer and acetate buffer, preferably from citrate buffer, phosphate buffer and phosphate-citrate buffer, or a mixture of these buffers. Most preferably, the buffer agent is monosodium citrate ($C_3H_4OH(COOH)_2COONa$). The monosodium citrate may be anhydrous, or may be monohydrate, dihydrate or trihydrate.

Advantageously, the use of citrate buffer obviates the requirement for pH adjustment using alkali (e.g. NaOH) and/or acid (e.g. HCl). Accordingly, the method may be devoid of a pH adjustment step using alkali (e.g. NaOH) and/or acid (e.g. HCl). The formulation may be devoid of alkali (e.g. NaOH) and/or acid (e.g. HCl).

The amount buffer agent, in particular of monosodium citrate in the final formulation may be (w/v) 0.05%, 0.07%, 0.1%, 0.15%, or a value in the range between any two of the aforementioned values, preferably between 0.05% and 0.1%, preferably about 0.07%. The mass ratio (w/w) of the buffer agent:paracetamol, for instance of sodium citrate:paracetamol is preferably 0.05 to 0.1:1, preferably 0.07:1.

The when the buffer agent is anhydrous monosodium citrate, the amount in the final formulation may be (w/v) 0.04%, 0.05%, 0.06%, 0.07%, 0.09%, 0.10%, 0.14%, 0.15%, or a value in the range between any two of the aforementioned values, preferably between 0.05% and 0.1%, preferably about 0.06%. The mass ratio (w/w) of the monosodium citrate monohydrate:paracetamol, for instance is preferably 0.04 to 0.8:1, preferably about 0.06:1.

The when the buffer agent is monosodium citrate monohydrate, the amount in the final formulation may be (w/v) 0.05%, 0.07%, 0.10%, 0.15%, or a value in the range between any two of the aforementioned values, preferably between 0.05% and 0.1%, preferably about 0.07%. The mass ratio (w/w) of the monosodium citrate monohydrate:paracetamol, for instance is preferably 0.05 to 0.1:1, preferably about 0.07:1.

The when the buffer agent is monosodium citrate dihydrate, the amount in the final formulation may be (w/v) 0.05%, 0.08%, 0.010%, 0.11%, 0.15%, 0.16%, or a value in the range between any two of the aforementioned values, preferably between 0.05% and 0.1%, preferably about 0.08%. The mass ratio (w/w) of the monosodium citrate monohydrate:paracetamol, for instance is preferably 0.05 to 0.1:1, preferably about 0.08:1.

The when the buffer agent is monosodium citrate trihydrate, the amount in the final formulation may be (w/v) 0.05%, 0.06%, 0.07%, 0.08%, 0.10%, 0.12%, 0.15%, 0.17%, or a value in the range between any two of the aforementioned values, preferably between 0.05% and 0.1%, preferably about 0.08%. The mass ratio (w/w) of the monosodium citrate monohydrate:paracetamol, for instance is preferably 0.05 to 0.1:1, preferably about 0.08:1.

Preferably the molar ratio of sodium citrate:paracetamol is 0.455:1. The sodium citrate is preferably monosodium sodium citrate, anhydrous, monohydrate, dihydrate or trihydrate, The present formulations for injection further contain an isotonic agent, intended to create an osmotic pressure in the region of that of physiological saline. The isotonic agent also referred to as isotonic agent herein may be a polyol, a sugar, a linear or cyclic glucitol having from 2 to 10 carbon atoms selected from mannitol, sorbitol, inositol, glucose and glycerol. This isotonic agent may be chosen from sodium chloride and glucose. A preferred isotonic agent is sodium chloride. The amount of isotonic agent, in particular of sodium chloride in the final formulation may be (w/v) 0.5%, 0.7%, 1%, 1.5%, or a value in the range between any two of the aforementioned values, preferably between 0.5% and 1%, preferably about 0.7%. The mass ratio (w/w) of the isotonic agent:paracetamol, for instance sodium chloride:paracetamol is preferably 0.5 to 1:1, preferably 0.6 to 0.8:1, preferably 0.7:1.

In a preferred embodiment, the aqueous solvent comprises water, an isotonic agent and a buffer agent, wherein the isotonic agent is sodium chloride and the buffer agent is sodium citrate. Preferably the amount of sodium citrate in the final formulation is about 0.07% (w/v), and the amount of sodium chloride in the final formulation is 0.7% (w/v). More in particular, the amount of monosodium citrate anhydrous is preferably about 0.06%, or the amount of monosodium citrate monohydrate is preferably about 0.07%, or the amount of monosodium citrate dihydrate is preferably about 0.08%, or the amount of monosodium citrate trihydrate is preferably about 0.08%.

Cysteine hydrochloride is added to the paracetamol solution under the conditions described to act as an anti-oxidising agent. The cysteine hydrochloride is preferably the monohydrate. The cysteine hydrochloride is added after the solution has cooled to a temperature of less than 38° C., preferably less than 38° C. and equal to or above 5° C., 10° C., 15° C., 20° C., 25° C., or 30° C.; preferably it is added immediately after such cooling. The addition is preferably rapid. The cooling may be or may not be active i.e. involve a cooling means. Preferably, the solution is left to cool towards ambient temperature. The cysteine hydrochloride is added without mechanical agitation such as stirring or shaking to prevent entry of oxygen into the solution.

After addition of cysteine hydrochloride, the air in the vessel is subsequently replaced with an inert gas (e.g. nitrogen or helium). The vessel is preferably subsequently closed and under placed under pressure of the inert gas. The mixture so formed is subsequently mechanically agitated under pressure of the inert gas. Mechanical agitation may proceed for about 5 minutes. Preferably, the solution is left to cool down towards ambient temperature during mechanical agitation.

The mass ratio (w/w) of cysteine hydrochloride:paracetamol is 0.010 to 0.040:1, preferably 0.020 to 0.030:1, preferably 0.025:1. For example, in a formulation and method as defined herein, cysteine hydrochloride may be present in the final formulation in an amount of 0.010%, 0.015%, 0.020%, 0.025%, 0.030%, 0.035%, 0.040%, 0.050%, 0.075% (w/v), or a value in the range between any two of the aforementioned values, preferably between 0.015% and 0.05%, preferably about 0.025% (w/v).

After step iv), the obtained solution may be filtered. Typically filtration takes place in a filtration unit. There filtration step may not be temperature regulated. It preferably takes place at a temperature of less than 38° C. Precautions may be taken for this purpose to replace the air in the filtration unit with an inert gas such as nitrogen, which gas will eventually be applied under pressure in the filtration unit to drive the solution across the filtration membrane. Eventually, the filling and packaging of the vials can also take place with the addition of an inert gas, such as nitrogen. The vials may be closed under vacuum. These bottles can be subsequently sterilised for 15 minutes at 121° C.

The formulation of the invention is generally prepared as follows. First an aqueous solvent or solution is prepared by mixing together water suitable for injection (WFI), a buffer and an isotonic agent, at a pH from 5 to 6 and preferably at a pH of about 5.5. Optionally one or more other water-miscible solvent(s), and/or surfactants might be present. Then, in a reaction vessel, paracetamol is admixed to the aqueous solvent, the solvent being provided at a temperature of between 65° C. and 95° C., preferably between 80° C. and 85° C. After paracetamol addition air in the reaction vessel is substituted by nitrogen and put under nitrogen pressure. The reaction is stirred. The solution is cooled to a temperature of less than 38° C., preferably less than 38° C. and equal to or above 5° C., 10° C., 15° C., 20° C., 25° C., or 30° C. Once cooled, cysteine hydrochloride monohydrate is added without mechanical agitation. The reaction vessel is closed, put under an atmosphere of nitrogen using filtered nitrogen gas (preferably filtered with a 0.22 μm filter) and mechanical agitation is performed. The pH is the solution is between 5.0 and 5.0, preferably between 5.4 and 5.6.

The invention also relates to a formulation as defined above that may be obtained via this process.

An important advantage of the present process comprises admixing of the paracetamol to the aqueous solvent that has a temperature of between 65° C. and 95° C., preferably between 80° C. and 85° C. cooling the solution so formed to a temperature of less than 38° C., preferably less than 38° C. and equal to or above 5° C., 10° C., 15° C., 20° C., 25° C., or 30° C. and adding cysteine hydrochloride without mechanical agitation. There is no requirement to purge the aqueous solvent of oxygen using, for example, nitrogen gas. Indeed, total absence of oxygen can never be ensured during all the preparatory steps such as filtration of the solution, and during filling into the vials. In presence of even traces of oxygen, two kinds of degradation products that can be generated:

due to heat action during sterilisation, a dimer of paracetamol may be formed. This dimer is a degradation product. This dimer is also significantly increased during storage of the product.

other unknown degradation products of paracetamol by oxidation are also generated during storage of the product.

Owing to the combination of steps, notably the temperature, cooling and cysteine, dimer formation is avoided during sterilisation, and increase of its level during storage is also avoided. As a consequence, the present formulation is different from those of the prior art insofar as stability is improved, dimer formation, and formation of other impurities is avoided. Thereby, the shelf-life of the product is increased.

Cysteine hydrochloride as anti-oxidant avoids the generation of the unknown degradation product of paracetamol by oxidation. It is added at a temperature of less than 38° C., preferably less than 38° C. and equal to or above 5° C., 10° C., 15° C., 20° C., 25° C., or 30° C. to avoid degradation of the cysteine hydrochloride at higher temperatures.

The use of sodium citrate as buffer further extends shelf life compared with buffering systems conventionally used such as phosphate.

The invention is described in greater detail in the examples below, which are given as non-limiting illustrations. In these examples, the temperature is room temperature or is expressed in degrees Celsius, and the pressure is atmospheric pressure. The water and all the reagents used are of injectable grade.

Moreover, all the examples form an integral part of the invention, as does any characteristic of the description including the examples, which appears to be novel with respect to any prior art, in the form of a general characteristic rather than of a particular characteristic of the example.

EXAMPLES

1. Preparation of a Liquid Pharmaceutical Formulation According to the Invention Formulations were prepared by admixing paracetamol to a solution of water for injection, buffer agent (monosodium citrate $H_2O$) and isotonic agent (sodium chloride), filtration and filling of glass vials or bottles. These bottles can then be sterilized for 15 minutes at 121° C.

Formulation 1

| Name of ingredient | Unit formula 100 ml | Formula per 1 ml |
|---|---|---|
| Paracetamol | 1.0 g | 10 mg |
| Sodium chloride | 700 mg | 7 mg |
| Sodium citrate H$_2$O | 70.0 mg | 0.70 mg |
| Cysteine hydrochloride monohydrate | 25.0 mg | 0.25 mg |
| Water For Injection | q.s. ad 100.0 ml | q.s. ad 1.0 ml |
| Nitrogen Low Oxygen | q.s. | q.s. |

The required tubes and filters are usually pre-sterilized at high temperatures and may be readily used at the above-mentioned temperature. The relevant manufacturing steps are performed quickly and without any unnecessary interruption in order to avoid contact of the solution with air and to keep the solution at the required temperatures e.g. between 80° C. and 85° C. for step i) and below 38° C. for step ii).

In a first step (comprising step i) a reaction vessel equipped with a stirrer is provided with about 90% of the total required quantity WFI (water for injection), which under some circumstances and preferably can be taken directly from a WFI loop at temperature between 80° C. and 85° C. The weights are registered. Then the following steps are performed: add smoothly and without mechanical agitation the required amount of NaCl and monosodium citrate H$_2$O. Air in the vessel is replaced with nitrogen, and is closed under nitrogen pressure. Stir the obtained mixture until complete dissolution (normally about 1 to 2 minutes). Reopen the vessel and measure the pH which should be between 5.0 and 6.0. pH measurement is performed within the vessel using a special electrode for pH measurement at temperature between 80° C. and 100° C. Once the pH has been confirmed, stop mechanically agitating the solution and add the required amount of paracetamol without mechanical agitation. Air in the vessel is replaced with nitrogen, and the vessel is closed under nitrogen pressure. Stir the obtained mixture until complete dissolution of paracetamol (about 1 minute) and bring quickly to final volume with WFI between 80° C. and 85° C. taking into consideration the density thereof. Stir for about 1 minute. Check the pH which will be between 5.0 and 6.0.

In a second step (step ii), the vessel is put under (0.22 µm filtered) nitrogen pressure and closed, while the temperature is dropped to a temperature of less than 38° C., preferably less than 38° C. and equal to or above 5° C., 10° C., 15° C., 20° C., 25° C., or 30° C. The temperature drop is preferably achieved by applying no or less heat, rather than using a cooling agent.

In a third step (step iii), the vessel is opened and the appropriate quantity of cysteine hydrochloride monohydrate is added. Air inside the vessel is replaced with nitrogen. The vessel is closed, and mechanical agitation continued at the same temperature used in step (ii). The temperature may be less than 38° C., preferably less than 38° C. and equal to or above 5° C., 10° C., 15° C., 20° C., 25° C., or 30° C. Mechanical agitation takes place under (0.22 µm filtered) nitrogen pressure.

The filtration of the solution need not be temperature regulated. A 0.22 µm filter with sanitary flange inlet and outlet connections and integral vent and drain valves for immediate installation can be used. The filtration vessel is certified for pressure and equipped with 0.22 µm vent filter and 0.22 µm nitrogen filter. Replace the air inside the filtration vessel by 0.22 µm filtered nitrogen and keep it under nitrogen pressure.

Connect the tube IN to the inlet flange of the filter and connect the other side of the tube to the compounding vessel. Connect the tube OUT to the outlet flange of the filter. Apply nitrogen pressure on the solution in the compounding vessel and discard about 300 ml of the solution by the tube that is connected to the outlet flange of the filter. Purge the filter by the drain valve and repeat this operation until no bubbles are present. Connect the tube OUT to the outlet flange of the filter to the filtration vessel. Apply nitrogen pressure on the solution in the compounding vessel to push the solution throughout the filter and open the valve of the vent filter of the filtration vessel. Achieve the filtration and stop the filtration when about 1 liter of solution is still remaining in the compounding vessel. Close off the valve of the vent filter of the filtration vessels and put it under (0.22 µm filtered) nitrogen pressure. Keep the solution in the filtration vessel until the temperature is about 25-27° C. or at room temperature. In this case, the vessel is kept until the next day. If the filtration vessel is equipped with a jacket, cool the solution and continue the operations. The special purging step in the process is preferred to minimize the risk of oxygenation of the mixture.

The filling of the solution was performed using known techniques by replacing the air in vials by (0.22 µm filtered) nitrogen until the nitrogen goes out of the needles of the foiling machine. Fill the solution under nitrogen flushing before and after filling.

Finally, the filled vials can be sterilized at 121° C. for 15 minutes.

2. Stability Measurements

Batches of the formulation according Example 1 are prepared as normal. Control batches in which certain components or steps are absent (e.g. cysteine hydrochloride absent) are also prepared. Each batch was stored at a temperature of 25° C.±2° C. at a relative humidity of 60%±5%. At various time intervals (0 months, 3 months, 6 months, 9 months, 12 months and 15 months) the batches are analysed for paracetamol content and for levels of impurities detectable by HPLC.

2.1 Analytical Method for Assaying Paracetamol Content by HPLC: (Eur. Ph. 2.2.29; 0049)

The analytical chromatographic conditions employed are as follows. Column: octylsilyl silica gel for chromatography R (5 µm), 25 cm×4.6 mm; temperature 35 C; detection: UV at 245 nm; flow rate: 1.5 ml/min; injection volume: 20 µl; run time: 15 minutes; mobile phase: mix 375 volumes of a 17.9 g/l solution of disodium hydrogen phosphate R, 375 volumes of a 7.8 g/l solution of sodium dihydrogen phosphate R and 250 volumes of methanol R containing 4.6 g/l of a 400 g/l solution of tetrabutylammonium hydroxide R. The test solution is 0.01 mg/ml of paracetamol in the mobile phase. Reference solution is a paracetamol working standard at a concentration of 0.01 mg/ml in the mobile phase. Resolution is a minimum 4.0 between the peaks due to impurity K and to paracetamol.

The content of paracetamol in the test solution is calculated by the area of the principal peak in the chromatogram of the test solution versus the area of the principal peak in the chromatogram of the reference solution taking into consideration the given purity of the used paracetamol working standard. Limits are 0.95 to 1.05 g/vial (95.0%-105.0%).

2.2 Analytical Method for Assay of Impurities by HPLC: (Eur. Ph. 2.2.29; 0049)

The analytical chromatographic conditions employed are the same as for assaying paracetamol content except that the runtime is 50 minutes (12 times the retention time of paracetamol). Test solution is used without dilution (10 mg/ml). Reference solution for system suitability and assay of impurities is prepared with 4-aminophenol R (impurity K), 4-nitrophenol (impurity F) and paracetamol working standard at 5 µg/ml of each. 10 mg of each substance is weighed and dissolved first in 20 ml flask into 10.0 ml of methanol and diluted with the mobile phase.

2.3 Calculations

The area related to each impurity in the reference solution is corrected according to each practical weight and each given impurity. Three types of impurity are measured ("K", "F", and "other" (unknown) impurities). The limits are given at 0.05% for impurity K, 0.05% for impurity F, and 0.10% for other impurities. For unknown impurities, only results >0.05% are reported.

For impurity K, the corrected area due to the peak of impurity K in the chromatogram of the reference solution is equivalent to 0.05% is assigned A1. Area due to the peak of impurity K in the chromatogram of the test solution is assigned A2. % of impurity K=(A2×0.05)/A1.

For impurity F, the corrected area due to the peak of impurity F in the chromatogram of the reference solution is equivalent to 0.05% is assigned A1. Area due to the peak of impurity F in the chromatogram of the test solution is assigned A2. % of impurity F=(A2×0.05)/A1.

For "other impurities", the corrected area due to the peak of paracetamol in the chromatogram of the reference solution is equivalent to 0.05% is assigned A1, area due to the peak of every unknown impurity in the chromatogram of the test solution is assigned A2, % of other impurities=(A2×0.05)/A1.

2.4 Results

After at least 15 months, there is no increase in impurities for batches containing cysteine hydrochloride, indicating an expected shelf life of at least 24 months. In the same period, there is an increase in impurities measured for batches without cysteine hydrochloride, indicating an expected shelf life of not more than 18 months.

What is claimed is:

1. Formulation that is stable to oxidation and hydrolysis, based on paracetamol in an aqueous solvent comprising:
    between 0.25% and 2% (w/v) paracetamol,
    between 0.5% and 0.9% (w/v) sodium chloride,
    between 0.05% and 0.09% (w/v) monosodium citrate monohydrate,
    between 0.015% and 0.035% (w/v) cysteine hydrochloride monohydrate, and
    water for injection,
    where the final pH of the formulation is between 5.0 and 6.0, and
    wherein the water for injection is not degassed by bubbling with an inert gas, prepared according to a method comprising in given order the steps of:
    (i) dissolving paracetamol in an aqueous solvent comprising an isotonic agent that is sodium chloride and a buffer agent that is sodium citrate, having a temperature between 65° C. and 95° C. and having pH between 5.0 and 6.0 in a reaction vessel,
    (ii) replacing the remaining air in the vessel by an inert gas and cooling the solution so formed to a temperature below 38° C.,
    (iii) adding cysteine hydrochloride to the solution without mechanical agitation, and
    (iv) closing the reaction vessel and mechanically agitating the solution in a nitrogen atmosphere;
    wherein for at least 15 months from preparation impurity K<0.05%; impurity F <0.05%, as determined by HPLC at 245 nm.

2. The formulation of claim 1, wherein the determination of impurities by HPLC is performed under the following conditions:
    octylsilyl silica gel column for chromatography,
    temperature of 35° C.,
    flow rate of 1.5 ml/minute, and
    mobile phase comprising disodium hydrogen phosphate, sodium dihydrogen phosphate, methanol, and tetrabutylammonium hydroxide.

3. A method of preparing the formulation of claim 1, comprising the following steps in given order:
    (i) dissolving paracetamol in an aqueous solvent comprising an isotonic agent that is sodium chloride and a buffer agent that is sodium citrate, having a temperature between 65° C. and 95° C. and having pH between 5.0 and 6.0 in a reaction vessel,
    (ii) replacing the remaining air in the vessel by an inert gas and cooling the solution so formed to a temperature below 38° C.,
    (iii) adding cysteine hydrochloride to the solution without mechanical agitation, and
    (iv) closing the reaction vessel and mechanically agitating the solution in a nitrogen atmosphere.

4. The method according to claim 3, wherein the aqueous solvent and/or solution is not purged with an inert gas.

5. The method according to claim 4, wherein the inert gas is nitrogen.

6. The method according to claim 3, wherein the aqueous solvent has a temperature between 70° C. and 90° C.

7. The method according to claim 3, wherein the aqueous solvent has a pH between 5.6 and 5.7.

8. The method according to claim 3, wherein the paracetamol is added to the aqueous solvent in step (i) without mechanical agitation.

9. The method according to claim 3 wherein the solution is stirred after replacing the remaining air in the vessel by the inert gas such as nitrogen in step (ii).

10. The method according to claim 3 wherein the solution in step (iv) is subsequently filtered prior to packaging in one or more vials.

11. The method according to claim 10, wherein the vials are closed under vacuum.

* * * * *